(12) United States Patent
Sexton et al.

(10) Patent No.: US 9,307,758 B2
(45) Date of Patent: *Apr. 12, 2016

(54) POLYACRYLAMIDE BASED AGRICULTURAL COMPOSITIONS

(75) Inventors: Franklin E. Sexton, Richmond, IL (US); Ryan T. Strash, Trevor, WI (US); Todd J. O'Connell, Wonder Lake, IL (US)

(73) Assignee: Exacto, Inc., Sharon, WI (US)

( * ) Notice: Subject to any disclaimer, the term of this patent is extended or adjusted under 35 U.S.C. 154(b) by 236 days.

This patent is subject to a terminal disclaimer.

(21) Appl. No.: 12/487,710

(22) Filed: Jun. 19, 2009

(65) Prior Publication Data

US 2014/0323609 A1  Oct. 30, 2014

(51) Int. Cl.
*C09K 17/00* (2006.01)
*A01N 25/04* (2006.01)
*A01N 25/30* (2006.01)

(52) U.S. Cl.
CPC .............. *A01N 25/04* (2013.01); *A01N 25/30* (2013.01)

(58) Field of Classification Search
CPC ...................................................... C08F 20/56
USPC .......................................................... 523/132
See application file for complete search history.

(56) References Cited

U.S. PATENT DOCUMENTS

| | | | |
|---|---|---|---|
| 3,346,494 A | 10/1967 | Robbins et al. | |
| 3,624,019 A | 11/1971 | Anderson et al. | |
| 4,052,353 A | 10/1977 | Scanley | |
| 4,413,087 A | 11/1983 | Bernot | |
| 4,681,912 A | 7/1987 | Durand et al. | |
| 4,696,962 A | 9/1987 | Danner et al. | |
| 4,904,695 A | 2/1990 | Bell | |
| 4,915,859 A * | 4/1990 | Kerr et al. | 508/257 |
| 4,956,399 A * | 9/1990 | Kozakiewicz et al. | 523/223 |
| 5,037,653 A | 8/1991 | Dawson | |
| 5,037,654 A | 8/1991 | Puritch et al. | |
| 5,292,800 A * | 3/1994 | Moench et al. | 524/801 |
| 5,490,943 A | 2/1996 | Eicken et al. | |
| 5,549,840 A * | 8/1996 | Mondin et al. | 510/365 |
| 5,587,357 A * | 12/1996 | Rhinesmith | 510/417 |
| 5,656,289 A * | 8/1997 | Cho et al. | 424/455 |
| 5,763,530 A * | 6/1998 | Chen et al. | 524/521 |
| 5,811,383 A * | 9/1998 | Klier et al. | 510/417 |
| 5,952,398 A | 9/1999 | Dietz et al. | |
| 6,025,432 A | 2/2000 | Ryan | |
| 6,110,981 A | 8/2000 | Davies et al. | |
| 6,143,830 A | 11/2000 | Utz et al. | |
| 6,172,031 B1 | 1/2001 | Stevens | |
| 6,326,013 B1 | 12/2001 | Lemann et al. | |
| 6,410,605 B1 | 6/2002 | Shimada et al. | |
| 6,475,974 B1 | 11/2002 | Leboucher et al. | |
| 6,686,417 B1 | 2/2004 | Reekmans et al. | |
| 6,709,716 B2 * | 3/2004 | Uy et al. | 427/505 |
| 6,803,345 B2 | 10/2004 | Herold et al. | |
| 6,835,761 B2 | 12/2004 | Harrison | |
| 7,074,752 B2 * | 7/2006 | Gordon | 510/492 |
| 2003/0147825 A1 | 8/2003 | Chiarelli et al. | |
| 2004/0194658 A1 | 10/2004 | Konno et al. | |
| 2005/0101510 A1 * | 5/2005 | Mondin et al. | 510/475 |
| 2005/0118210 A1 | 6/2005 | Kachi et al. | |
| 2005/0234166 A1 | 10/2005 | Lau | |
| 2005/0239957 A1 * | 10/2005 | Pillsbury et al. | 524/801 |
| 2006/0004130 A1 | 1/2006 | Strominger et al. | |
| 2006/0289137 A1 | 12/2006 | Gelman et al. | |
| 2007/0049496 A1 | 3/2007 | Messerschmidt et al. | |
| 2007/0197418 A1 | 8/2007 | Rahse | |
| 2007/0219315 A1 | 9/2007 | Braun | |
| 2010/0037513 A1 * | 2/2010 | Petrucci | C10L 10/12 44/301 |
| 2013/0231429 A1 | 9/2013 | Sexton | |
| 2014/0323312 A1 | 10/2014 | Sexton et al. | |
| 2014/0378554 A1 | 12/2014 | Sexton et al. | |

FOREIGN PATENT DOCUMENTS

| | | |
|---|---|---|
| CN | 101933509 A | 1/2011 |
| KR | 20000068408 A | 11/2000 |
| WO | WO 8810274 | 12/1988 |
| WO | WO 2005/077336 A1 | 8/2005 |

OTHER PUBLICATIONS

Flick, E.W., Cosmetics Additives—An Industrial Guide, 1991, William Andrew Publishing/Noyes, p. 401, 412.*
Applied Polymer systems, Inc., APS 600 Series Silt Stop, Applied Polymer Systems, Inc., 2002, 2 pages, http://www.siltstop.com/silt_stop_aps_600.html.
Lentz et al., "Field REsults Using Polyacrylamide to Manage Furrow Erosion and Infiltration", Soil Science, Oct. 1994, vol. 158, Issue 4, Abstract http://journals.lww.com/soilsci/Abstract/1994/10000/FIELD_RESULTS_USING_POLYACRYLAMIDE_TO_MANAGE.7.aspx.
Polyacrylamide (PAM) Definition, pp. PM-1-PM-5. http://www.michigan.gov/documents/deq/nps-polyacrylamide_332130_7.pdf, published 2010.
Flick, E.W., Industrial Surfactants, 1993, Noyles Publications, Second Edition, p. 240.
International Search Report, PCT/US2013/034468, Dec. 16, 2013, 3 pages.

* cited by examiner

*Primary Examiner* — David Karst
(74) *Attorney, Agent, or Firm* — Berenato & White, LLC

(57) ABSTRACT

A polyacrylamide based agricultural composition as a microemulsion is provided in form of a water-in-oil microemulsion with polyacrylamide dissolved in the water phase where the polyacrylamide solids content is from about two up to about 15 percent by weight, which is then further diluted in water at the time of use to impart the desired characteristics of the polymer to the water phase or to the material to which the water phase is applied.

26 Claims, No Drawings

POLYACRYLAMIDE BASED AGRICULTURAL COMPOSITIONS

This invention relates to a polyacrylamide based agricultural compositions and more particularly to a polyacrylamide based agricultural compositions as a microemulsion.

BACKGROUND OF THE INVENTION

Water-soluble polymers are long known to be very useful in both agricultural and industrial applications. Among the polymers that are extremely well known, belongs the class of water-soluble polymers known as linear polyacrylamides. They are very useful because of their superior properties of infinite solubility and low use rates, among others. By far, the major use for linear polyacrylamides is in the treatment of water, especially wastewater.

In wastewater treatment and uses like canal sealing, polyacrylamide flocculates, or agglomerates to form particles. This flocculation, where light particles are attracted together to form heavier particles, causes them to sink rather than float, clarifying the water containing the particles. In agricultural sprays, the ability of these polymers to retain water, control movement and add viscosity is utilized to enhance the effectiveness of the sprays, in addition to other purposes.

These linear polyacrylamides are commonly available in three commercial forms. First, as a water-dispersible solid, polyacrylamides are used in applications such hydroseeding and canal sealing. This form slowly dissolves in water, but has a tendency to agglomerate when added too quickly or all-at-once to water. When this happens, the lumps that are formed take hours, days or weeks to dissolve in water. This slow dissolution property is used to advantage in the applications specified, but is a highly undesirable trait in situations that require quick dispersion of the polymer.

Second, water-dispersed polymers are used, which have the distinct advantage of already being dissolved. It is used in agricultural spray deposition aids, among others. However, not much polymer can be dissolved in water, only up to about two (2%) percent, before the solution becomes too viscous to be handled easily. This material also generates a lot of expense due to the shipping of mostly water, thus creating great inefficiency.

The third historical form is an emulsion, more specifically a water-in-oil emulsion. This is a polyacrylamide, with the polyacrylamide chains contained in small droplets of water, that are dispersed in an oil, by using emulsifiers to help make the two phases mix. Emulsions are droplets or "bubbles" of liquid, known to those practiced in the art as "micelles", suspended in another liquid with which the first liquid will not mix. The micelles are often called the "discontinuous phase" and the suspending liquid is called the "continuous phase".

In the case of polyacrylamide emulsions, the polymer, polyacrylamide, is dissolved in the discontinuous phase, in this case the water phase; and the continuous phase is oil. This is known as a water-in-oil (W/O) emulsion or a reverse emulsion. This type of emulsion keeps the polymer in small packets of water, which burst open when the emulsion comes in contact with water. Polyacrylamide emulsions disperse well in water with vigorous stirring and are used prevalently in water treatment.

Such emulsions are also used, among other things, in pesticide tank mixtures to aid in preventing drift and increasing deposition on target species. The problems with emulsions are that they form clumps, like solid forms, when the emulsion is added to water with little or no agitation or if the water to emulsion ratio is too low. Also, emulsions are inherently unstable and will eventually break or separate into oil and water layers. The oil rises as a layer, and the water layer sinks. Then since the polymer chains are now free to combine, because they are not separated by the oil "walls" (that is the oil and water separation or dividing line), they combine and form large lumps.

The polyacrylamide polymer itself comes in several types, defined by electrical charge of the polymer chain. It can be nonionic, anionic or cationic. The cationic form is commonly used in water treatment. In the agricultural applications, the cationic, or positively charged polymer, is rarely used, as it has a deleterious effect on aquatic wildlife. The nonionic or uncharged form is a reaction product of pure acrylamide, forming an uncharged, but water-soluble polymer that is quite inert in the environment.

Acrylamide is co-reacted with other monomers to form the cationic or anionic forms. To form the anionic polymer, acrylamide is most often reacted with an acrylate monomer that is further reacted so that it becomes negatively charged. The nonionic and anionic polymers have different properties. At lower levels in water, the anionic polymers build properties such as viscosity faster that are more desirable. Anionics are compatible with other charged molecules such as are contained in fertilizers. However, they can react undesirably with certain other charged molecules. Thus, nonionic polyacrylamides are used in situations where the anionics are incompatible with other molecules.

The amount of charge is measured as a percent of the comonomer added. Thus, a polyacrylamide that is 30% acrylate and 70% acrylamide is called a 30 percent-charged polymer. This percentage may be expressed as weight or mole percent, depending on the manufacturer. Typically, if the polymer is a combination of the two monomers, the acrylic acid portion is reacted with base to form the acid salt. The polymer is then considered to be charged.

Microemulsions are a very recent, commercially available development. A microemulsion is a special type of emulsion. These microemulsions have the same basic structure as traditional emulsions, except that the droplets are smaller. Smaller droplets, by virtue of the solution physics involved, are very stable and the droplets do not combine or separate in solutions as traditional emulsions do. Microemulsions are also virtually clear, while sometimes having only a slight haze, as opposed to a standard emulsion, which is milky white.

Microemulsions, as they are now, do have their own drawbacks, however. The biggest drawback to a microemulsion is that, if it is combined with water or aqueous solutions, microemulsions will form a skin at its surface that drastically reduces the water diffusion; and the diffusion of oil or emulsifier combination into the water phase. This is due to the fact that there are very many small aqueous droplets near the surface of the emulsion and when they are combined with water, water diffuses quickly across the discontinuous phase and swells the micelles nearest the surface. The micelles swell, combine, burst and rupture, in that order.

This instantaneous bursting of many of the droplets entangles the polymer on the surface of the microemulsion and forms a barrier, which, in turn, slows diffusion of water further into the microemulsion and dispersion of the rest of the polymer. This phenomenon, sometimes known as a "skin", causes the same problems that traditional emulsions have in terms of dispersion and clean out.

Observers of microemulsions may actually observe that they are clear and therefore question the ability of the product to do the job intended or the presence, in this case, of polymer until the product is added to water and the characteristic milky appearance and slimy feel of polyacrylamide emulsion added to water appears.

While each of the polymers and the delivery systems have distinct advantages, certain applications create great disadvantage for all polymers. For instance, in fields that are watered using pivot irrigation, the polymer is known to have been tested and shown to be effective at reducing the need for water. However, handling of the traditional emulsion, which is, thus far, the only economical form for this application, can plug pumps, nozzles, screens, or other apparatus, when the clean out procedures are not followed properly because of the lumping process described above. Microemulsions are tested in this process and found to have the same problems because of the skinning process described. The current invention addresses many of these problems.

SUMMARY OF THE INVENTION

Among the many objectives of the present invention is the provision of a microemulsion of polyacrylamide that disperses easily in water, does not clump and is stable for long periods of time that is then dispersed in a water medium.

Another objective of the present invention is the provision of a solution for emulsion dispersion problems by using a more dilute version, in terms of polyacrylamide content of the microemulsion with a set of stabilizing and dispersing ingredients that slows bursting of the bubbles into aqueous solution, thus allowing the individual bubbles to disperse into the water phase with its oil coating before bursting.

Also, an objective of the present invention is the provision of a concentrated solution rather than a water-dispersed polymer of polyacrylamide.

Moreover, an objective of the present invention is the provision of and easy dispersing formula of polyacrylamide.

A further objective of the present invention is the provision of an inherently stable formula of polyacrylamide.

A still further objective of the present invention is the provision of polyacrylamide having relative ease of hydration of the dilute polymer solution.

These and other objectives of the invention (which other objectives become clear by consideration of the specification and claims as a whole) are met by providing a polyacrylamide based agricultural composition as a microemulsion.

DESCRIPTION OF THE PREFERRED EMBODIMENTS

The invention is a mixture including a water-in-oil microemulsion with polyacrylamide dissolved in the water phase where the polyacrylamide solids content is from about two up to about 15 percent parts by weight, which is then further diluted in water at the time of use to impart the desired characteristics of the polymer to the water phase or to the material to which the water phase is applied. More preferably, the range of polyacrylamide solids content is about two percent to about 14 percent by weight. Most preferably, the range of polyacrylamide solids content is about four percent to about 12 percent by weight.

The current invention further contains two specifically important ingredients. First, it contains at least one fatty acid. Second, it contains at least one nonionic surfactant. These two ingredients work together to stabilize the emulsion. The ingredients all come together to form an easily water dispersible product with fewer handling issues. The terms "surfactant" and "emulsifier" may typically be used interchangeably, since all emulsifiers are surfactants and most surfactants are emulsifiers.

This effective use of fatty acids is surprising, because it is known that ionic surfactants do not stabilize water-in-oil (W/O) emulsions well. The book "Chemistry and Technology of the Cosmetics and Toiletries Industry", D. F. Williams, W. H. Schmitt, Second Ed., Springer, 1996. pg. 31, states that "A limited number of W/O emulsifiers are available. This is because ionic emulsifiers will not work in the case of W/O emulsions." Since fatty acids can form, and often are used as, negatively charged species, it is considered an ionic emulsifier.

Preferably the fatty acids include at least one selected from the group consisting of C8 to C30 fatty acids. Such acids include, but are not limited to myristic, lauric, palmitic, stearic, oleic, and linoleic acids and mixtures of fatty acids derived from natural sources such as coco, lauryl, palm, soy, cottonseed and tall oil fatty acids. More preferably, fatty acids whose major content is C12 to C18 fatty acids such as coco, lauryl, palm, soy, cottonseed and tall oil fatty acids. Most preferably, fatty acids whose major content is C18 fatty acids such as soy and tall oil fatty acids. Preferably, the fatty acid content is up to about 20 percent by weight. More preferably, the range of fatty acid content is about two percent to about 14 percent by weight. Most preferably, the range of fatty acid content is about two percent to about 13 percent by weight.

Preferably the nonionic surfactants include at least one surfactant selected from the group consisting of ethoxylated surfactants, nonylphenol ethoxylates or alcohol ethoxylate or other ethoxylated surfactants. Better results are obtained with nonylphenol ethoxylates or alcohol ethoxylates. The best results are obtained with most preferably alcohol ethoxylates. Preferably, the nonionic surfactant content is up to about 20 percent by weight. More preferably, the range of nonionic surfactant content is about two percent to about 14 percent by weight. Most preferably, the range of nonionic surfactant content is about two percent to about 13 percent by weight.

The other surprising property of the nonionic surfactant ingredient in this invention is the use of a nonionic surfactant with a hydrophilic-lipophilic balance (HLB) greater than 9.3. More preferably the hydrophilic-lipophilic balance (HLB) is about 9.4 to 20. Most preferably the hydrophilic-lipophilic balance (HLB) is about 9.4 to 15. As stated, previous inventions used nonionic surfactants with an HLB of 9.3 or less. However, this invention requires the use of a nonionic surfactant with at least some portion of the nonionic surfactant having the higher HLB.

The microemulsion can be achieved in either of two ways. One way is to classically create the microemulsion using well-known techniques. These techniques are often employed in manufacturing these microemulsions. However, the objective is almost always to create a microemulsion with the highest content of active ingredient possible. Thus, these microemulsions are classically more than 15% polyacrylamide for economy of transport and value.

This application requires less content be present because the bubbles must be allowed to disperse in the water phase, and this occurs poorly in mixtures having greater than 15 percent by weight solids. So forming less polymer during manufacturing is one way to achieve the goal.

However, the other way is to dilute the commercially available material with more oil and emulsifier. The commercially available microemulsion is inexpensive compared to the cost of a special reaction. The dilution is relatively simple and inexpensive, while effectively reaching the same objectives at less cost.

The charge of the polyacrylamides in the current invention is from zero to 40 percent because the reaction starts with zero to 40 percent acrylic acid or acid salt. The polymer that is formed with acrylic acid or an acid salt monomer is called anionic polyacrylamide since the polymer itself contains a negative charge, which is balanced by a cation, usually sodium. The polymer where little or no acid or acid salt is used is considered to be nonionic polyacrylamide because the polymer contains essentially no charge. The range of charge is necessary to ensure compatibility of the polymer with the various types of ingredients in tank mixes. Higher or lower charge directly affects compatibility, with the higher charge generally being more compatible with fertilizers, and the lower charge being more compatible with other types of charged species that might form an insoluble salt.

The molecular weight of the polymer is anywhere up to 35 Megagrams per mole. More preferably molecular weight of the polymer is up to 30 Megagrams per mole. Most preferably molecular weight of the polymer is about one to about 25 Megagrams per mole. This property allows for the maximum flexibility in the use of the polymer. Ultra-high molecular weight polymers build viscosity quickly and are highly stable in the soil, both of which are desirable properties for the uses enumerated. The variability in charge allows use of the polymer with many different kinds of materials.

Beyond the polymer, the rest of the system provides a mechanism for delivering the polymer, and appears to have some effect on characteristics of the polymer. This part of the invention that is especially unique and unexpected. This set of ingredients allows for a lower amount of the water phase and a higher amount of the oil phase and, therefore, better dispersion into water.

In order for these two phases to mix or "emulsify", a set of emulsifiers are used. These are molecules that have a specific structural requirement. Emulsifiers must contain two areas within the molecule, one that is hydrophobic or water-hating and one that is hydrophilic or water-loving. This structure acts as the glue that holds the two immiscible phases together, by going to the interface between the two phases and laying across that interface with the hydrophobic part sticking into the oil phase and the hydrophilic part sticking into the aqueous phase.

The emulsifiers used in the current invention are a combination of fatty acids and nonionic surfactants. This combination is unique in its ability to bring the two phases together. The fatty acids are a very low HLB emulsifier and the nonionic surfactants used are a moderate to high HLB emulsifier. The presence of the fatty acids are necessary in terms of dispersion as it is the main contributor to slowing the diffusion of water and, therefore, the bursting of droplets into the water phase.

The benefit of this invention is twofold. First, the microemulsion is more stable than normal emulsions, as stated above. This makes long-term storage problems, which can be an issue with emulsions, possible and even likely. The second benefit, and another major feature of this invention, is the level of polymer and the solution in which it is delivered.

The level of polymer must be economically viable. Delivering a solution that is too low in polymer means delivering too much water or other ineffective material to a site, thereby causing shipping costs to rise.

However, a polymer level that is too high, in this case, can be detrimental, as well. It is well known to users that handle emulsions, that adding a small amount of water to any emulsion breaks the emulsion and causes it to gel. This gelling forms a large, thick mass that does not dissolve easily in water and which may have to be stirred for days in order to dissolve completely. The lower level of polymer combined with the other elements significantly reduces this gelling.

The current invention addresses the problem of formation of the microemulsion "skin" by production of a dilute, but not too dilute, and stable microemulsion. This is accomplished, in a practical and economic sense, through dilution of the microemulsion with oil. The addition of oil creates a thicker continuous layer through which water and water droplets must pass. This slows diffusion of water from the bulk liquid into the droplets. The micelles, therefore, swell more slowly. Slower dispersion of the droplets at the surface of the microemulsion and slower swelling of the droplets in the microemulsion means that the surface skin does not form when the microemulsion comes in contact with water.

However, addition of oil to the microemulsion, alone, is not adequate. If oil is added directly to a typical manufactured polyacrylamide microemulsion, or any emulsion, for that matter, an unstable emulsion results and discontinuous layer separates from the continuous layer. The addition of further ingredients, typically more emulsifier, is necessary to ensure a stable, easy dispersing, polyacrylamide microemulsion.

The current invention addresses the potential instability by addition of emulsifiers to form stable microemulsions. These emulsifiers must balance between the water and oil phases and be compatible with the emulsifiers that are typically used in microemulsions. This balance is typically achieved in microemulsions very well. However, with the addition of more oil in the case of the current invention, the balance of the emulsifiers must be adjusted to coincide with the water/oil ratio change.

The level of fatty acid and surfactants needed to create the stable microemulsions varies depending on the ratio of oil to aqueous phase and also on the level of polymer present in the aqueous phase. The level of fatty acid runs from 0.01 to 10 percent to form a stable microemulsion in the current invention. However, the fatty acid cannot be added alone. It must be balanced with surfactants to make it more compatible with the aqueous phase.

In the current invention, the addition of supplementary nonionic surfactant is required. Probably the most important reason for the use of additional surfactants is that the addition of fatty acid throws off the balance between the water and oil phases, also called the hydrophilic and lipophilic phases, respectively, of the surfactant package. The result is that it is necessary to add something that, while it is still a surfactant, counteracts or balances the hydrophobic nature of the fatty acid. This is accomplished in the current invention through the use of nonionic surfactants with a medium to high hydrophilic-lipophilic balance or HLB.

Typical oils used in addition to fatty acids are defined as 1) petroleum oils, more preferably paraffinic oils, or 2) naturally occurring oils such as seed oils like cottonseed, canola, soybean, corn, palm kernel or coconut oil, or 3) derivatives of naturally occurring oils such as the methyl or ethyl esters of the above named oils. The petroleum or paraffinic oils are preferred, as well as methyl ethyl esters of the above named oils, for use in the composition of this invention. The oils, taken singly or in mixtures as named, herein comprise up to about 60 percent by weight of the composition. More preferably, the oils, taken singly or in mixtures as named, herein comprise up to about 55 percent by weight of the composition. Most preferably, the oils, taken singly or in mixtures as named, herein comprise about 10 percent to about 55 percent by weight of the composition.

HLB is the nature of a surfactant to balance between aqueous and nonaqueous phases. A low HLB surfactant has a high affinity for oily or nonaqueous phases and is highly insoluble in water. A high HLB surfactant has a high affinity for water and forms clear mixtures with water even at high concentrations. Fatty acids have a long lipophilic chain terminated in a carboxylic acid moiety that is hydrophilic. The lipophilic portion dominates the molecule, however. Nonionic surfactant has a carefully controlled HLB and range across the entire spectrum of HLB. Addition of the proper nonionic surfactant allows the correct HLB of the overall surfactant package to be reached.

Thus, the proper mixture is reached for the current invention by the formation of a microemulsion with the addition of fatty acids and nonionic surfactant with the levels of each carefully controlled.

The current invention carefully controls the level of oil, level and type of surfactant and level of polymer to provide an economical, easy-to-handle solution. The invention disperses well in water, but not too well. The skinning, lumping and clumping that is a problem with other microemulsions and standard emulsions does not form. Yet there is enough surfactant for the product to disperse into the water phase through a mechanism that releases the water droplets into the added water more slowly. This slower release probably allows the polymer to disperse into the water to which it is added before other water droplets nearby in the microemulsion burst open or combine, thereby avoiding the entanglement that normally causes skinning or lumps.

Also, the invention appears even clearer, in terms of appearance, than other emulsions or microemulsions. Microemulsions typically have only a slight haziness. They can be seen through easily but do have minor, but definitive, cloudiness. The current invention is crystal clear in its most stable form. The clarity is achieved through the unique combination of ingredients that is added beyond those that are normally present in the microemulsion.

The microemulsion disperses into aqueous phase well because of the combination of oil and surfactants that surround the water droplets that contain the polymer. If the amount and/or ratios of oil and surfactants are not correct, either one of two things can happen.

First, if the mixture contains too much oil phase, the dispersion of polymer into the water will be slowed. Aside from this physical problem, there are also financial problems with too much oil phase, as well.

Microemulsions formed using too much oil will not have a viscosity issue, as the aqueous solutions of polyacrylamide do, but will become uneconomical for the same reason that the aqueous polymer solutions will be uneconomical. There will be too little active ingredient shipped, and, additionally, the solution surrounding the polymer would be more expensive than just plain water.

Second, if enough oil phase is not added or the oil/emulsifier ratio is too high in the amount of emulsifier or the emulsifier is too water soluble, the droplets will swell and burst open too quickly causing the problems of skinning and lumping. After the stable microemulsion is produced, the product is utilized by diluting the product in water or water-based mixtures for application.

The current invention's ability to be used properly is greatly enhanced over other forms. The microemulsion may be added to any aqueous solution with a modicum of stirring or movement. It will disperse well, not forming lumps or clumps. The means of addition may be in the form of pouring, as into a container or tank, or by injection, as into a pipeline using a pump and check valve, or by any other means of addition where the microemulsion is dispersed into an aqueous liquid.

There are multiple uses for the current invention. The basic idea is to disperse the invention in an aqueous media when it is ready to be used.

One use is in irrigation. The invention is pumped, using some sort of injection pump of piston or other design, into a pipe carrying irrigation water to a pivot or other delivery system. Because of the superior dispersion characteristics of the invention, there is no need to further treat or add other ingredients. The injection is followed directly by a water rinse. The water rinse easily moves through the pump, without any complications.

Another use is in waterways as a canal sealing agent. While emulsions and solids have been used in the past, the handling of the materials is clearly problematic.

Still, another use is in an agricultural or non-agricultural spray tank mix containing pesticides. It can be added directly into the tank while the ingredients in the tank are being stirred. Again, the dispersion is very easy, not forming lumps or clumps.

The current invention may also be used in pesticide tank mixes for several reasons. The first reason is that it provides the ability to control deposition of a pesticide to a target species. The presence of a deposition aid or drift control product will be required in the future in order to control drift onto non-target species.

The composition may be put into an aqueous medium in order to impart the desired properties. The aqueous medium is then used in a desired fashion. Such uses include, but are not limited to, applying the microemulsion to at least one seed, at least one growing crop, at least one patch of bare ground, at least one roadside, at least one industrial area, at least one right-of-way, at least one forest area, at least one turf or other vegetation, at least one soil, at least one waterway, at least one crop, at least one water management area or combinations thereof.

Forming the aqueous dispersion is accomplished in any suitable fashion. Typical forming processes include, but are not limited to, forcing the composition into the aqueous medium by at least one operation selected from the group consisting of stirring the aqueous medium and the composition, pumping the aqueous medium and the composition through a pipe or stirring it in a tank, pouring the composition into a tank containing the aqueous media and injecting the composition into the tank.

In the following examples, which are intended to illustrate without unduly limiting the scope of this invention, all parts and percentages are by unless otherwise indicated.

Example 1

The following ingredients are assembled:
Hydro treated, paraffinic oil 69.3%
A flocculating agent 19.8% (such as Superfloc® E 4366 U.S. Trademark Registration Number 0748648)
Tall oil fatty acids 4% Nonylphenol ethoxylate 6 mole 2.9% Nonylphenol ethoxylate 9 mole 4%.

The ingredients are added to a container in the order specified above.

The mixture is stirred continuously while the ingredients are added. A crystal clear mixture is formed. This mixture is dispersed in an agricultural tank mix containing water, pesticide and fertilizer. It is found to increase average droplet size and decrease small droplets, thus reducing drift from the tank when compared to the same agricultural tank mix without the above mixture.

The current invention delivers polyacrylamide, a proven deposition aid or drift control agent, in a form that is stable for long periods of time and mixes well in most tank mixes. The second reason is to deliver a combination of oil and drift control agent in the correct ratio for both to be effective. This combination, thus far, is deliverable in one bottle using polyacrylamide as the deposition aid. The current invention makes this combination possible. These are but a few uses and, thus, the utility of this invention is many-fold.

This application—taken as a whole with the abstract, specification, and claims—provides sufficient information for a person having ordinary skill in the art to practice the invention disclosed and claimed herein. Any measures necessary to practice this invention are well within the skill of a person having ordinary skill in this art after that person has made a careful study of this disclosure.

Because of this disclosure and solely because of this disclosure, modification of this composition and method tool can become clear to a person having ordinary skill in this particular art. Such modifications are clearly covered by this disclosure.

What is claimed and sought to be protected by Letters Patent is:

1. An agricultural water-in-oil microemulsion composition having a weight and comprising:
   up to about 15 percent by weight, based on the weight of the agricultural water-in-oil microemulsion composition, of polyacrylamide polymer or copolymer solids,
   up to about 20 percent by weight, based on the weight of the agricultural water-in-oil microemulsion composition, of at least one fatty acid, and
   up to about 20 percent by weight, based on the weight of the agricultural water-in-oil microemulsion composition, of at least one nonionic surfactant having a combined hydrophilic-lipophilic balance of greater than 9.3, and oil,
   wherein, when said agricultural water-in-oil microemulsion composition is diluted by water or water-based mixtures to form a diluted product, the composition disperses without lumps or clumps in the water or water-based mixtures.

2. An agricultural water-in-oil microemulsion composition according to claim 1 wherein the polyacrylamide polymer or copolymer solids are present in an amount of from about 4 to about 12 percent by weight, based on the weight of the agricultural water-in-oil microemulsion composition.

3. An agricultural water-in-oil microemulsion composition according to claim 1 wherein the polyacrylamide polymer is a nonionic polyacrylamide.

4. An agricultural water-in-oil microemulsion composition according to claim 1 wherein the polyacrylamide copolymer is an anionic polyacrylamide.

5. An agricultural water-in-oil microemulsion composition according to claim 4 wherein the anionic polyacrylamide is derived from acrylamide and sodium acrylate.

6. An agricultural water-in-oil microemulsion composition according to claim 1 wherein the polyacrylamide copolymer is an anionic polyacrylamide with up to about 40 percent anionic content.

7. An agricultural water-in-oil microemulsion composition according to claim 1 wherein the polyacrylamide polymer or copolymer solids comprises an anionic polyacrylamide having a 20 to 40 percent anionic content.

8. An agricultural water-in-oil microemulsion composition according to claim 1 wherein the at least one fatty acid is present in an amount of from about 2 to about 5 percent by weight, based on the weight of the agricultural water-in-oil microemulsion composition.

9. An agricultural water-in-oil microemulsion composition according to claim 1 wherein the at least one fatty acid is primarily C18 unsaturated fatty acids.

10. An agricultural water-in-oil microemulsion composition according to claim 1 wherein the at least one fatty acid is tall oil fatty acid.

11. An agricultural water-in-oil microemulsion composition according to claim 1 wherein the at least one nonionic surfactant is an ethoxylated surfactant.

12. An agricultural water-in-oil microemulsion composition according to claim 1 wherein the at least one nonionic surfactant is nonylphenol ethoxylate, fatty alcohol ethoxylate or a combination thereof.

13. An agricultural water-in-oil microemulsion composition according to claim 1 wherein the at least one nonionic surfactant is fatty alcohol ethoxylate.

14. An agricultural water-in-oil microemulsion composition according to claim 1 wherein the at least one nonionic surfactant is present in an amount of about 9 to about 20 percent by weight, based on the weight of the agricultural water-in-oil microemulsion composition.

15. An agricultural water-in-oil microemulsion composition according to claim 1 wherein about 8 percent to about 70 percent by weight of the at least one nonionic surfactant has a hydrophilic-lipophilic balance above 9.3.

16. An agricultural water-in-oil microemulsion composition according to claim 1 wherein the oil is a paraffinic oil, a natural oil or a derivative of a natural oil.

17. An agricultural water-in-oil microemulsion composition according to claim 1 wherein the oil is a paraffinic oil.

18. A process of dispersing a composition into an aqueous media comprising:
   a) providing an agricultural water-in oil microemulsion composition comprising up to about 15 percent by weight, based on the weight of the agricultural water-in-oil microemulsion composition, of polyacrylamide polymer or copolymer solids, up to about 20 percent by weight, based on the weight of the agricultural water-in-oil microemulsion composition, of at least one fatty acid, up to about 20 percent by weight, based on the agricultural water-in-oil microemulsion composition, of at least one nonionic surfactant having a combined hydrophilic-lipophilic balance of greater than 9.3, and oil;
   b) forcing the agricultural water-in-oil microemulsion composition into an aqueous medium to form a diluted product without lumps or clumps in the aqueous medium;
   c) allowing the micelles to burst into the aqueous medium; and
   d) applying the agricultural water-in-oil microemulsion composition with burst micelles to a desired or intended target.

19. A process according to 18 wherein said forcing the agricultural water-in-oil microemulsion composition into the aqueous medium comprises at least one operation selected from the group consisting of stirring the aqueous medium and the agricultural water-in-oil microemulsion composition, pumping the aqueous medium and the agricultural water-in-oil microemulsion composition through a pipe or stirring it in a tank, pouring the agricultural water-in-oil microemulsion composition into a tank containing the aqueous medium, and injecting the agricultural water-in-oil microemulsion composition into the tank containing the aqueous medium.

20. A process according to claim 19 further comprising applying the agricultural water-in-oil microemulsion composition to at least one seed, at least one growing crop, at least one patch of bare ground, at least one roadside, at least one industrial area, at least one right-of-way, at least one forest area, at least one turf or other vegetation, at least one soil, at least one waterway, at least one crop, at least one water management area or combinations thereof.

21. An agricultural water-in-oil microemulsion composition having a weight and comprising:
   up to about 15 percent by weight, based on the weight of the agricultural water-in-oil microemulsion composition, of polyacrylamide polymer or copolymer solids,
   up to about 20 percent by weight, based on the weight of the agricultural water-in-oil microemulsion composition, of at least one fatty acid of C8 to C30,
   up to about 20 percent by weight, based on the weight of the agricultural water-in-oil microemulsion composition, of at least one nonionic surfactant having a combined hydrophilic-lipophilic balance of greater than 9.3, and
   up to about 60 percent by weight, based on the weight of the agricultural water-in-oil microemulsion composition, of oil,
   wherein, when said agricultural water-in-oil composition is diluted by water or water-based mixtures to form a diluted product, the composition disperses without lumps or clumps in the water or water-based mixtures.

22. An agricultural water-in-oil microemulsion composition according to claim 21 wherein:
   a) the polyacrylamide polymer or copolymer solids is present in a content of about 4 to about 12 percent by weight, based on the weight of the agricultural water-in-oil microemulsion composition;
   b) the at least one fatty acid of C12 to C18 is present in a content of about two percent to about 14 percent by weight, based on the weight of the agricultural water-in-oil microemulsion composition;
   c) the at least one nonionic surfactant is present in a content of about two percent to about 14 percent by weight, based on the weight of the agricultural water-in-oil microemulsion composition; and
   d) the oil is present in a content of up to about 55 percent by weight, based on the weight of the agricultural water-in-oil microemulsion composition.

23. An agricultural water-in-oil microemulsion composition according to claim 22 wherein:
   a) the at least one fatty acid includes at least one member selected from the group consisting of coco fatty acid, lauryl fatty acid, palm fatty acid, soy fatty acid, cottonseed fatty acid and tall oil fatty acid;
   b) the content of the at least one at least one nonionic surfactant is about two percent to about 13 percent by weight, based on the weight of the agricultural water-in-oil microemulsion composition;
   c) the at least one nonionic surfactant has a hydrophilic-lipophilic balance of about 9.4 to about 15; and
   d) the at least one nonionic surfactant is at least one surfactant selected from ethoxylated surfactants.

24. An agricultural water-in-oil microemulsion composition according to claim 23 wherein:
   the polyacrylamide polymer or copolymer solids has a charge from zero to 40 percent, based on the weight of the polyacrylamide polymer or copolymer solids; and
   the molecular weight of the polyacrylamide polymer or copolymer solids up to 35 Megagrams per mole.

25. An agricultural water-in-oil microemulsion composition according to claim 24 wherein:
   a) the at least one nonionic surfactant is at least one surfactant selected from the group consisting of nonylphenol ethoxylates and alcohol ethoxylates; and
   b) the oil is at least one oil selected from the group consisting of paraffinic oils, naturally occurring oils and derivatives of naturally occurring oils.

26. An agricultural water-in-oil microemulsion composition according to claim 25 wherein:
   a) the oil is at least one oil selected from the group consisting of cottonseed oil, canola oil, soybean oil, corn oil, palm kernel oil, coconut oil, and the methyl or ethyl ester thereof; and
   b) the oil is provided in a content of about 10 percent to about 55 percent by weight of the agricultural water-in-oil microemulsion composition.

* * * * *